(12) United States Patent
Zhu et al.

(10) Patent No.: US 11,746,368 B1
(45) Date of Patent: Sep. 5, 2023

(54) LACTOCOCCUS LACTIS SUBSP. LACTIS A32, DERIVED PRODUCT AND USE THEREOF

(71) Applicant: Qilu University of Technology, Shandong Province (CN)

(72) Inventors: Deqiang Zhu, Shandong Province (CN); Xinli Liu, Shandong Province (CN); Yujie Lian, Shandong Province (CN); Leshan Han, Shandong Province (CN); Shuo Peng, Shandong Province (CN)

(73) Assignee: QILU UNIVERSITY OF TECHNOLOGY, Shandong Province (CN)

( * ) Notice: Subject to any disclaimer, the term of this patent is extended or adjusted under 35 U.S.C. 154(b) by 0 days.

(21) Appl. No.: 17/902,330

(22) Filed: Sep. 2, 2022

(30) Foreign Application Priority Data

May 13, 2022 (CN) .......................... 202210533401.8

(51) Int. Cl.
    *C12N 1/20* (2006.01)
    *C12R 1/46* (2006.01)
    *C12P 21/02* (2006.01)

(52) U.S. Cl.
    CPC .............. *C12P 21/02* (2013.01); *C12N 1/205* (2021.05); *C12R 2001/46* (2021.05)

(58) Field of Classification Search
    None
    See application file for complete search history.

(56) References Cited

PUBLICATIONS

Khelissa et al. Archives of Microbiology. 2021, 203, pp. 465-480.*

* cited by examiner

*Primary Examiner* — Vera Afremova
(74) *Attorney, Agent, or Firm* — Muncy, Geissler, Olds & Lowe, P.C.

(57) ABSTRACT

The present invention provides a *Lactococcus lactis* subsp. *lactis* A32, derived product and use thereof, the present invention falls in the technical field of microorganisms. In the present invention, the *Lactococcus lactis* subsp. *lactis* A32 is obtainable by compound mutation on the basis of the original strain *L. lactis* lxl. Experiments showed that, compared with nisin titre of the original strain *L. lactis* lxl, the *Lactococcus lactis* subsp. *lactis* A32 has high nisin yield, and the nisin titre has been improved for 3~4 times (over 5066.58 IU/mL); in the meanwhile, the growth curve of the *Lactococcus lactis* subsp. *lactis* A32 is slightly longer than the original strain *L. lactis* lxl and biomass peaks of them are basically consistent. The present invention has laid a foundation for large scale production of nisin.

9 Claims, 3 Drawing Sheets

LACTOCOCCUS LACTIS SUBSP. LACTIS A32, DERIVED PRODUCT AND USE THEREOF

TECHNICAL FIELD

The present invention belongs to the technical field of microorganisms, specifically *Lactococcus* subsp. *Lactis* A32, derived product and use thereof.

BACKGROUND TECHNOLOGY

Nisin is also called *Lactococcus lactis*, and is a kind of metabolite produced by the bacterium *Lactococcus lactis* and capable of inhibiting growth of other *lactobacillus* first proposed by Rogers in 1928. In 1933, Whitehead et al discovered that two strains of lactic streptococci produced some substance that very strongly inhibited the growth of other strains and prohibited formation of acids, verified that the strains exhibit features of proteins, and guessed that the strains are probably a kind of polypeptide. Since 1944, Mattick has been devoted to researches of this substance, subsequently, he found that nisin production capacities of different *streptococcus* strains were apparently different, screened out bacterial species with high nisin yield, and prepared and purified the polypeptide, as the inhibitory substance was generated in group N streptococci, the substance was named N-inhibitor substance, abbreviated as nisin, also called *Lactococus lactis*.

In 1928, the division of dairy research laboratories of the bureau of dairy industry, U.S. department of Agriculture reported inhibitory effects of streptococci on *Lactobacillus bulgaricus*; in 1953, NISAPLIN was released on the market, and commercial application of nisin was started; in 1969, Food and Agriculture Organization of the United Nations, World Health Organization and Joint FAO/WHO Expert Committee on Food Additives have sequentially approved use of nisin as additives in food industry. Thereafter, nisin has played an important role in preservation of food such as dairy products, canned food, drinks and meat products during their manufacturing, transportation and storage, waste caused by deterioration of cereals is reduced and food transportation distance is prolonged, and nisin has been widely used in more than one hundred countries and regions all over the world as food preservatives.

With development of the society and economy, pursuit for life of higher quality and healthy food grows stronger, conventional preservatives have triggered more and more safety and health concerns, *Lactococcus lactis* as biological preservatives has attracted more and more attention. As internationally recognized safe and poison free natural preservatives, efficient synthesis of nisin has always been a hot spot in the field; furthermore, due to good biological safety of nisin, researches on use values of nisin have gone beyond food preservation.

Demands for nisin from the food industry and medical industry are growing, however, currently there is a lack of literature on bacterial strains having high nisin yield.

SUMMARY OF THE INVENTION

In view of the situation, the present invention aims to provide a *Lactococcus lactis* subsp. *Lactis* A32, derived product and use thereof, the strain A32 has not only very good genetic stability, but also has very high nisin yield.

The present invention provides a *Lactococcus lactis* subsp. *Lactis* A32, and a deposit number of the *Lactococcus lactis* subsp. lactic A32 is GDMCC No. 62395.

The present invention provides a microbial inoculum for producing nisin, wherein active ingredients of the microbial inoculum comprise *Lactococcus lactis* subsp. *lactis* A32.

The present invention provides use of the *Lactococcus lactis* subsp. *lactis* A32 or the microbial inoculum in nisin production.

Preferably, resistance of the *Lactococcus lactis* subsp. *lactis* A32 to nisin is 15000 IU/mL.

Preferably, nisin titre produced by the *Lactococcus lactis* subsp. *lactis* A32 is over 5066.58 IU/mL.

The present invention provides a method for producing nisin based on the *Lactococcus lactis* subsp. *lactis* A32, comprising following steps:

Inoculating bacterial liquid of activated *Lactococcus lactis* subsp. *lactis* A32 into a fermentation medium for fermentation and culturing, collecting fermentation liquid and separating nisin.

Preferably, the fermentation medium is a CM1 medium.

Preferably, an inoculation amount of the bacterial liquid is 8%~15%.

Preferably, temperature for fermentation and culturing is 28~32° C.

Preferably, time for fermentation and culturing is 20~40 h.

Deposit number of the *Lactococcus lactis* subsp. *lactis* A32 provided in the present invention is GDMCC no. 62395. The *L. lactis* A32 is obtained by compound mutation on the basis of initial *L. lactis* subsp. *lactis* lxl. Experiments showed that, the *L. lactis* subsp. *lactis* A32 has a high nisin production capability, nisin titre is over 5066.58 IU/mL, and is 3~4 times of nisin titre of the initial *L. lactis* subsp. *lactis* lxl; in the meanwhile, a growth curve of the *Lactococcus lactis* subsp. *lactis* A32 is slightly later than that of the initial strain *L. lactis* lxl, the stationary phase started at 12 h, and the biomass peaks are consistent.

SURVIVAL INFORMATION REGARDING DEPOSITED MICROBIAL MATERIALS

Figure 1:
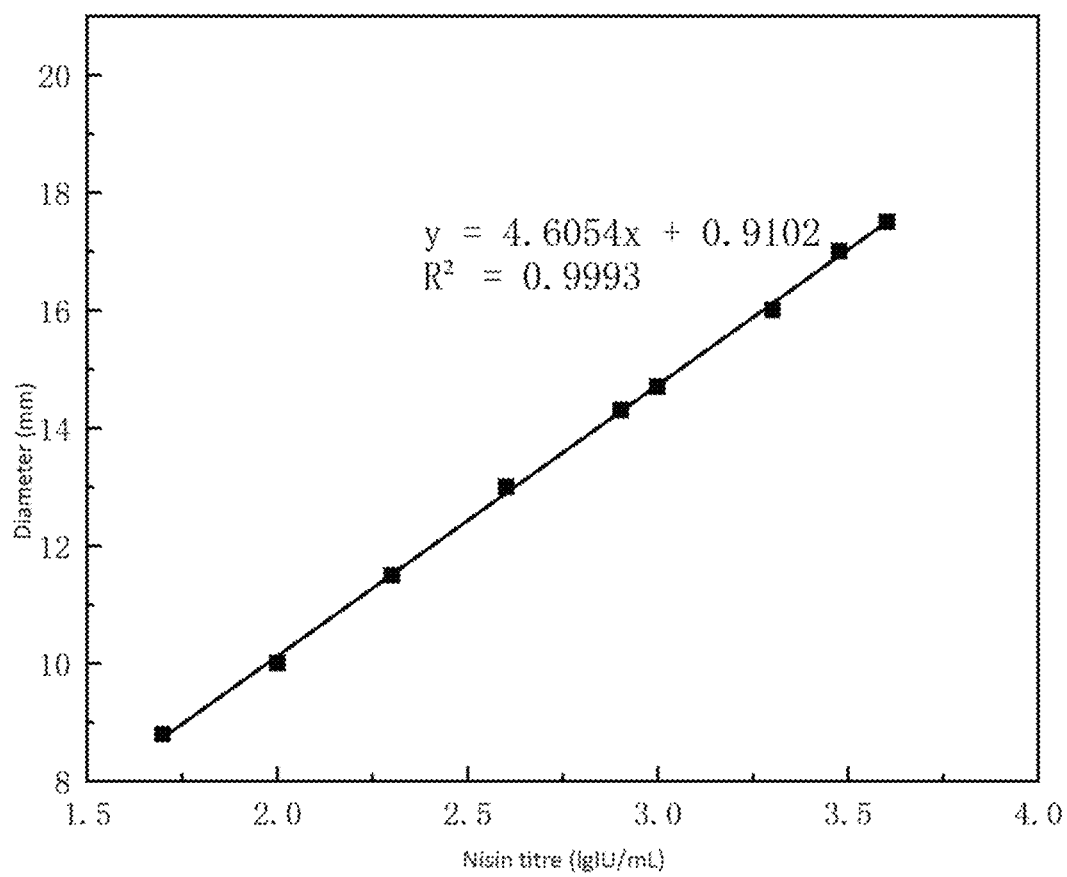
FIG. 1 shows a nisin titre standard curve.

*Lactococcus lactis* subsp. *Lactis* A32 is deposited in Guangdong Microbial Culture Collection Center, abbreviated as GDMCC, having a place of business at Institute of Microbiology, Guangdong Academy of Sciences, 5th floor, experimental building, no. 100, Xianlie Middle Road, Yuexiu District, Guangzhou, Guangdong 236494 China, deposit time is Apr. 18, 2022, deposit number is GDMCC No. 62395, and strain number is A32.

EMBODIMENTS

The present invention provides a *Lactococcus lactis* subsp. *Lactis* A32, deposit number of the *Lactococcus lactis* subsp. *lactis* A32 is GDMCC 62395.

In the present invention, two highly productive strains A32 and A225 are obtained by atmospheric room temperature plasma and compound mutation by UV light of initial strain *L. lactis* lxl, and the yield has been increased for 2 times. Upon genetic stability test, the strain A225 is not genetically stable, mutant strains with apparent reverse mutation appeared during culturing; for strain A32, there is no apparent reverse mutation, nisin titre is very stable, and the strain A32 is deposited for subsequent production.

In the present invention, upon comparative genome analysis between the *Lactococcus lactis* subsp. *lactis* A32 and the initial strain lxl, compared with the *L. lactis* lxl, 107 genes in the A32 genome were mutated, comprising 39 single-nucleotide polymorphisms (SNPs), 34 insertion mutations and 34 deletion mutations. According to annotated results, some mutated genes have definite functions, some mutated genes are related to energy metabolism, for example, rexB, ftsH, gntP and yfmR etc; some mutated genes are related to ion transport, for example yfmR, rbcR, zitR, adcA and copB; some mutated genes are related to DNA replication, transcription and translation, for example dnaG, rpsI, rex, and arlR; some mutated genes are related to amino acid transport and metabolism, for example patM, tcyC, tcyJ, cysS, and brnQ, however, functions of most mutated genes are unknown.

In the present invention, an amplification culture method of the preserved *Lactococcus lactis* subsp. *lactis* A32 comprises preferably the following steps: Obtaining seed solution by streak culture and seed culture of the preserved *Lactococcus lactis* subsp. *Lactis* A32;

Inoculating the seed solution into a CM1 liquid fermentation medium, culturing for 12~14 h, and obtaining the *Lactococcus lactis* subsp. *Lactis* A32.

In the present invention, the culture medium for streak culture and seed culture is a GM17 medium. Temperature for streak culture and seed culture is preferably 28~32° C., more preferably 30° C. Culturing time for streak culture and seed culture is preferably 10~12 h. The seed culture is preferably shaking culture. A rotation speed of shaking culture is preferably 180~220 rpm, and more preferably 200 rpm. The present invention provides a microbial inoculum for nisin production, wherein active ingredients of the microbial inoculum comprise the *Lactococcus lactis* subsp. *Lactis* A32.

In the present invention, the microbial inoculum further comprises auxiliary materials.

In the present invention, no special limitation is given to types of the auxiliary materials, and auxiliary materials for microbial inoculum well-known in the art can be used. In the present invention no special limitation is given to preparation method of the microbial inoculum, and the preparation method used for making microbial inoculum well-known in the art can be used.

The present invention provides use of the *Lactococcus lactis* subsp. *lactis* A32 or the microbial inoculum in nisin production.

In the present invention, resistance the *Lactococcus lactis* subsp. *lactis* A32 to nisin is 15000 IU/mL. Nisin titre of the *Lactococcus lactis* subsp. *lactis* A32 is preferably 5066.58 IU/mL.

The present invention provides a method for producing nisin with the *Lactococcus lactis* subsp. *lactis* A32, comprising the following steps:
inoculating activated *Lactococcus lactis* subsp. *lactis* A32 into a fermentation culture medium for fermentation and culture, collecting fermentation solution and separating nisin.

In the present invention, the fermentation culture medium is preferably a CM1 medium. In embodiments of the present invention, the CM1 medium comprises preferably the following contents and ingredients: sucrose 10 g/L, peptone 10 g/L, yeast extract 10 g/L, $KH_2PO_4$ 10 g/L, NaCl 2 g/L, $MgSO_4$ 0.2 g/L, and pH 6.8. In the present invention, an inoculating amount of the microbial liquid is preferably 8%~15%, more preferably 10%~12%. Temperature for fermentation and culturing is 28~32° C. and more preferably 30° C. Fermentation and culturing time is preferably 20~40 h, more preferably 28~35 h, and most preferably 30 h.

In the present invention, maximal biomass in the fermentation solution is consistent with the maximal biomass in the original strain lxl, however, by measuring nisin titre of the fermentation solution, it turned out that, with extension of fermentation time, nisin titre rised gradually, and peaked at around 28 h, thereafter, with extension of the fermentation time, nisin titre reduced gradually and was far higher than the nisin titre of the original strain lxl. This showed that nisin accumulated during growth phase of A32 was advantageous compared with the original strain lxl.

Hereinafter, the *Lactococcus lactis* subsp. *lactis* A32, derived product and use thereof provided in the present invention will be described in details, however, the description shall not be construed as limitations to the protection scope of the present invention.

Embodiment 1

Mutation Screen Experiment

*L. lactis* lxl was used as a starting strain and mutated by respectively ARTP and UV mutation, two strains were screened out, which were named respectively *L. lactis* A32 and *L. lactis* A225. The A32 and the A225 were respectively seed cultured and inoculated into a CM1 medium (sucrose 10 g/L, peptone 10 g/L, yeast extract 10 g/L, $KH_2PO_4$ 10 g/L, NaCl 2 g/L, $MgSO_4$ 0.2 g/L, pH 6.8, sterilizing at 121° C. for 20 min) and were cultured for 48 h, and nisin titre of the fermentation solution was obtained.

The method to measure nisin titre in the fermentation solution was to weight nisin standards 500 mg, dissolve the same in dilute HCl solution 100 mL with a concentration of 0.02 mol/L and obtain nisin solution with a concentration of 5000 IU/mL; dilute the nisin solution to respectively 50, 100, 200, 400, 800, 1000, 2000, 3000 and 4000 IU/mL; add the diluted solutions to small holes, culture at 37° C. for 18 h, at this time, obvious bacteriostatic circles appeared around the small holes that samples have been filled, diameters of the bacteriostatic circles were measured by a vernier caliper; the diameters of the bacteriostatic rings were used as a transverse coordinate and 1 g values of nisin titre were used as a longitudinal coordinate and a nisin titre standard curve was drawn (see FIG. 1). The concentrations (IU/mL) of nisin refer to valence of nisin, which is determined according to Chinese national standard GB 1886.231-2016.

The results were shown in table 1.

TABLE 1

| nisin titre of the mutant strains and the original strain | |
| --- | --- |
| Strain | Nisin titre (IU/mL) |
| Original strain lxl | 1603.06 |
| A32 | 5066.58 |
| A225 | 5385.14 |

From the foregoing results, it can be known that the two mutant strains had apparently higher nisin titre compared with the original strain, and the nisin titre was increased for 2~3 times.

The high-yield strains obtained during mutation screening were streaked at a solid GM17 plate at 30° C. and cultured for 24 h to form an F1 generation; one loop of the strains was picked for streaking on another solid GM17 plate at 30° C. for 24 h to form an F2 generation until an F20 generation. Single colonies were picked every three generations from the plates for activation, fermentation and culturing at 30° C. and 200 rpm, after centrifugation and the supernatant was collected to determine the nisin titre.

TABLE 2 genetic stability test results

| Generation Strain | F3 | F6 | F9 | F12 | F15 | F18 | F20 |
|---|---|---|---|---|---|---|---|
| A32 (IU/mL) | 5089 | 5081 | 5095 | 5109 | 5075 | 5083 | 5091 |
| A225 (IU/mL) | 2589 | 2481 | 2395 | 2309 | 2275 | 2183 | 2091 |

From the genetic stability test results, it can be known that A225 was not genetically stable, and the mutant phenotypes were apparently reversible; and A32 phenotypes were not apparently reversible, and A32 with stable nisin production capacity was preserved in a refrigerator at −80° C.

Embodiment 2

Bacteriostatic Circle Experiment of the Strain A32

(1) Streaking culture: the glycerin tube preserving the strain *L. lactis* A32 was taken from the −80° C. very low temperature refrigerator. The inoculation loop was sterilized by passing through a flame of an alcohol burner in an ultra-clean working bench, three-phase streaking was conducted at the GM17 solid plate, and then the strain 32 was put into a 30° C. constant temperature culture box in an inverted manner for 24 h;

(2) Seed culture: single colonies were picked from the streaked GM17 solid plate, the colonies were inoculated in a GM17 liquid culture medium (a 250 mL triangular flask with the volume of liquid 50 mL), and put into a 30° C. constant temperature shaker for culturing for 12 h at 200 rpm to form seed solution;

(3) Fermentation culture: the cultured seed solution was inoculated as per a 10% (V/V) inoculating amount into a 250 mL triangular flask containing CM1 liquid medium 50 mL, and put into a 30° C. constant temperature shaker for culturing for 24 h at 200 rpm, and the strain A32 fermentation liquid was obtained.

As per the foregoing method, fermentation liquid of the original strain *L. lactis* lxl was cultured. The supernatant of the A32 fermentation liquid and the original strain *L. lactis* lxl fermentation liquid was taken for bacteriostatic circle experiment and nisin titre thereof was obtained.

Specifically, methods for conducting the bacteriostatic circle experiments are as following: first of all, pouring a layer of agar culture media onto the plate to form the first layer of culture medium, after cooling and curing, putting Oxford cups at an even interval; adding activated experiment strains (the original strain *L. lactis* lxl or the strain A32) 0.2% (V/V) on the culture medium 51 after cooling to about 50° C., pouring the strains on the first layer of culture medium to form the second layer of culture medium, after cooling and curing, taking out the Oxford cups and uniform small holes were formed; adding the sample to be measured 200 μL into the small holes, culturing at 37° C. until apparent bacteriostatic circles were formed around the small holes, and diameters of the bacteriostatic circles were measured.

The results were shown in table 3

TABLE 3 bacteriostatic circle experiment for the original strain *L. lactis* lxl and the strain A32

| Strain | Diameter of bacteriostatic circle (mm) |
|---|---|
| A32 | 17.98 |
| Original strain lxl | 15.54 |

Embodiment 3

Researches on Resistance to Nisin of the Original Strain lxl and A32

First of all, a series of nisin concentrations were designed, a certain amount of nisin was weighed as per the series of nisin concentrations, diluted in sterile dilute hydrochloric acid 0.02 mol/L, mixed evenly, added onto the solid GM17 culture medium at 60° C., mixed evenly, and poured on the plate to form high concentration nisin gradient plate. Activated lxl or A32 was coated on the high concentration nisin gradient plate and put into a 30° C. constant temperature culture box in an inverted manner for culture, growth conditions of colonies on the plate were observed.

The results were shown in table 4

TABLE 4 resistance of the original strain *L. lactis* lxl and A32 to nisin

| Strain | Nisin resistance (IU/mL) |
|---|---|
| A32 | 15000 |
| Original strain lxl | 8000 |

Compared with the original strain lxl resistance of A32 to nisin is improved apparently, which also promises that A32 has high nisin yield.

Embodiment 4

Fermentation Comparison Experiment of Mutant Strain *L. lactis* A32 and the Starting Strain lxl As per the method used in embodiment 2, after activating, the *L. lactis* A32 and the original strain lxl were inoculated into CM1 for fermentation and culture for 48 h. Samples were taken every three hours, optical density was measured with an ultraviolet spectrophotometer at 600 nm, shown as $OD_{600}$; and nisin titre in the fermentation liquid was measured by bacteriostatic circle experiments.

Figure 2A:
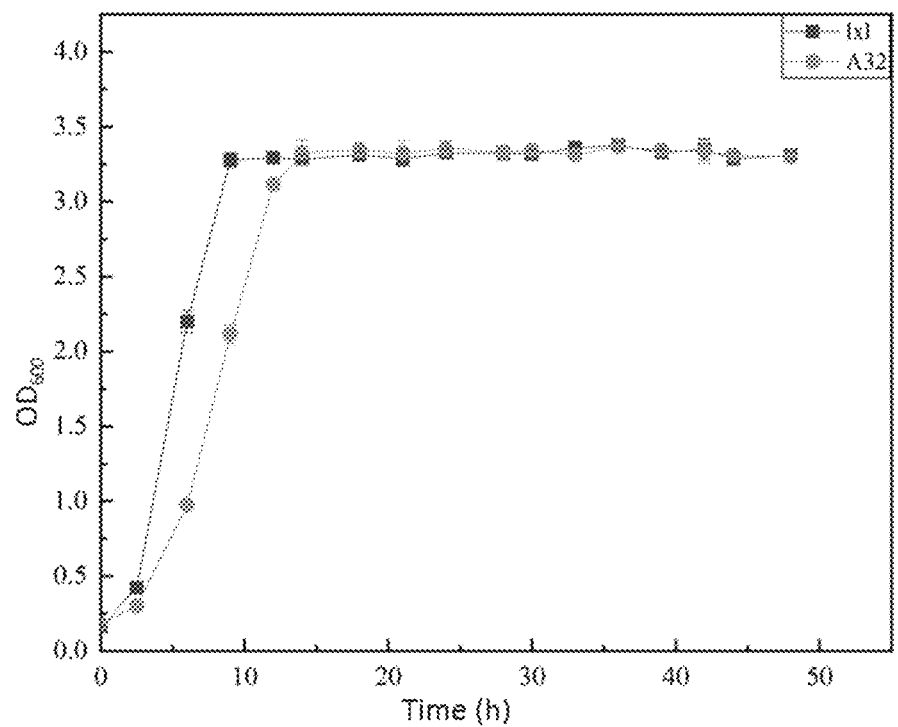
FIGS. 2A and 2B show diagrams of growth curves of A32 and lxl (FIG. 2A) and results of nisin titres (FIG. 2B)
Figure 2B:
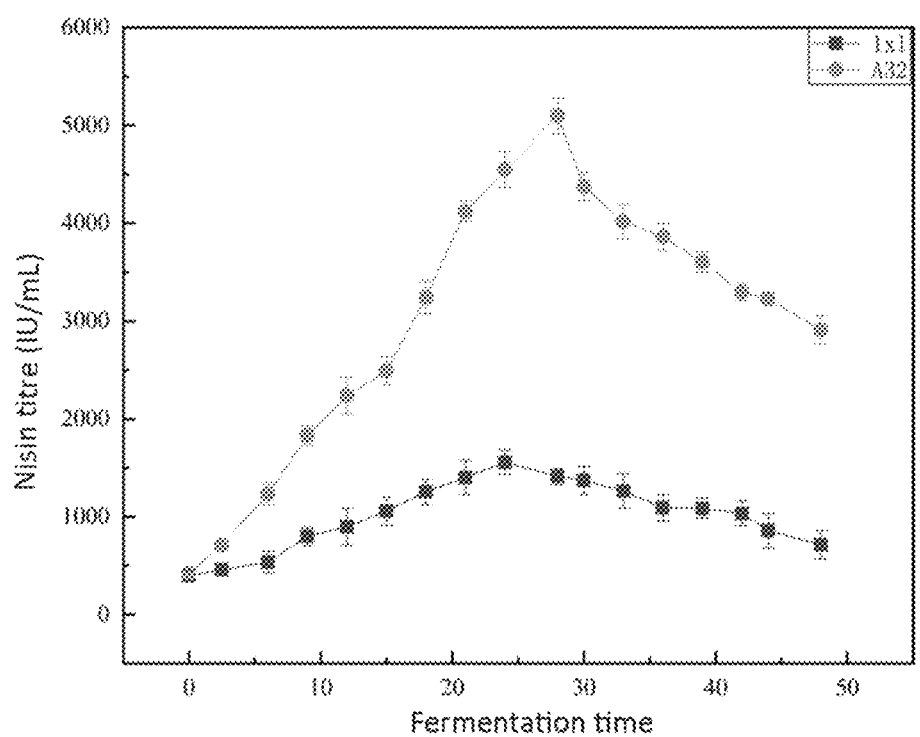

Results have been shown in FIGS. 2A and 2B.

Viewing from FIG. 2A, the growth curve of A32 was slightly later than the growth curve of the original curve lxl, the original strain lxl reached stationary phase at 12 h, and the OD600 peaks were substantially the same. From the foregoing results, it can be known that nisin accumulated during the growth phase of A32 was much more than lxl (see FIG. 2B).

Embodiment 5

Comparative Genomic Analysis of *L. lactis* A32 and lxl

Comparative genomic analysis was given to the mutant *L. lactis* A32 with high nisin yield and the original strain *L.*

*lactis* lxl, specifically, the comparative genomic analysis was completed by Guangzhou Gene Denovo Biotechnology Co., ltd.

Figure 3:
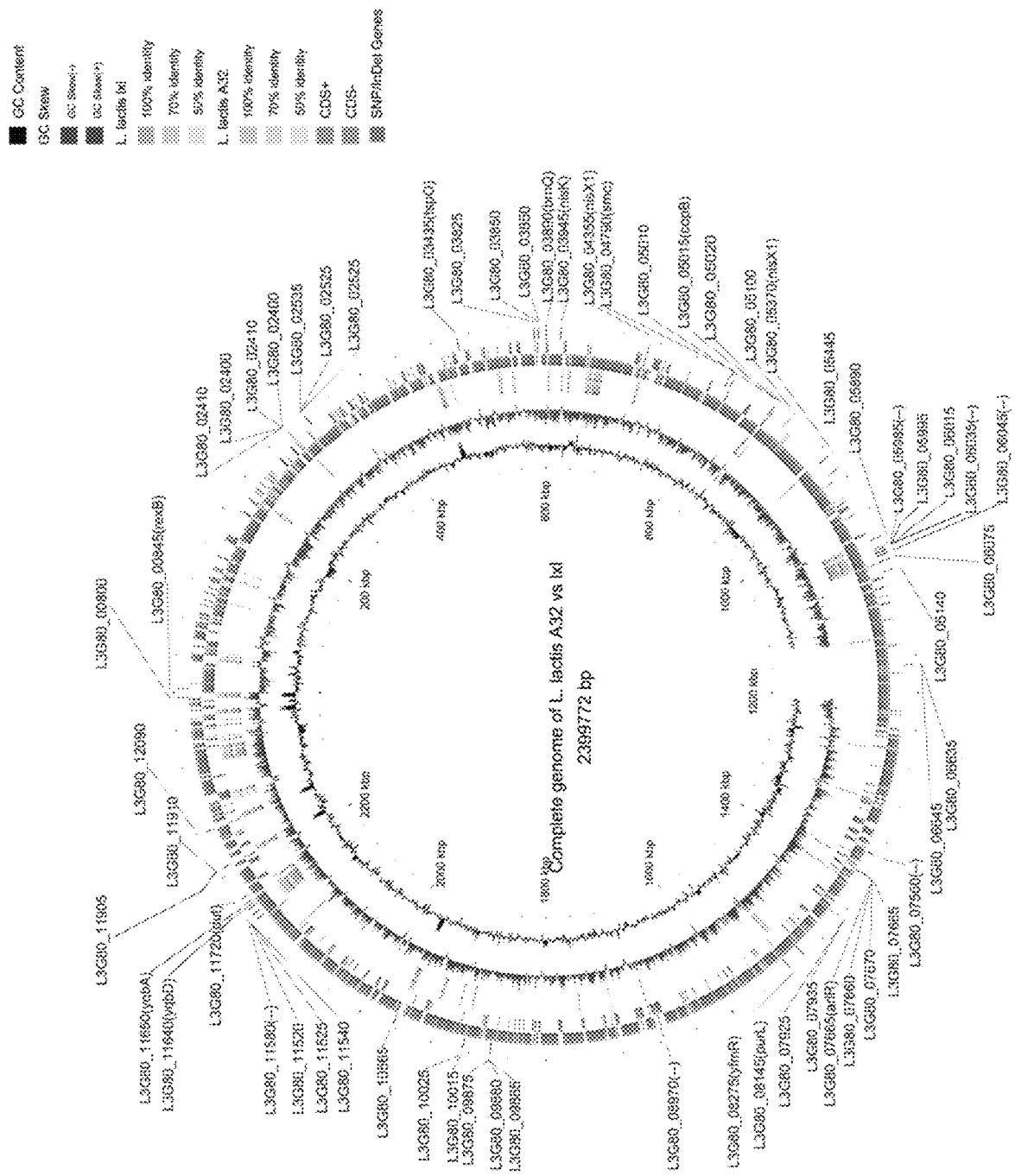
FIG. 3 shows analysis results of A32 and lxl by comparative genomics.

The sequencing results were shown in FIG. 3. Compared with genomic DNAs of *L. lactis* lxl, a total of 107 genes in the A32 genome were mutated compared with the lxl genome, including 39 single-base mutations, 34 insertion mutations and 34 deletion mutations, as shown in table 5. The sequences of the mutated genes were compared with the reference genome sequences in the NCBI database for COG functional annotations, some genes with base mutations had clear functions, some mutated genes, such as rexB, ftsH, gntP and yfmR, were related to energy metabolism; some mutated genes were related to ion transport, such as yfmR, rbcR, zitR, adcA and copB; to DNA replication, transcription and translation, such as dnaG, rpsI, rex and arlR; and to amino acid transport and metabolism, such as patM, tcyC, tcyJ, cysS and brnQ while functions of some genes were unknown.

| Gene IP | Name | Mutation type | COG Functional Description |
|---|---|---|---|
| L3G80_00845 | rexB | SNP | ATP-dependent nuclease, subunit B |
| L3G80_00940 | ftsH | SNP | ATP-dependent Zn proteases |
| L3G80_09890 | cysS | SNP | Cysteinyl-tRNA synthetase |
| L3G80_00020 | gntP | Ins | H+/gluconate symporter and related permeases |
| L3G80_08275 | yfmR | Ins | ATPase components of ABC transporters with duplicated ATPase domains |
| L3G80_05905 | dut | DEL | dUTPase |
| L3G80_11910 | ccpB | DEL | Bata-glucosidase/6-phospho-beta-glucosidase/ beta-galactosidase |
| L3G80_00735 | rpsI | SNP/Del | Ribosomal protein S9 |
| L3G80_08145 | purL | SNP | Phosphoribosylformylglycinamidine (FGAM) synthase, synthetase domain |
| L3G80_05450 | patM | SNP | ABC-type amino acid transport system, permease component |
| L3G80_05455 | tcyC | SNP | ABC-type polar amino acid transport system, ATPase component |
| L3G80_05445 | tcyJ | SNP | ABC-type amino acid transport/signal transduction systems, periplasmic component/domain |
| L3G80_11520 | adcA | SNP | ABC-type metal ion transport system, periplasmic component/surface adhesion |
| L3G80_03200 | tig | SNP | FKBP-type peptidyl-prolyl cis-trans isomerase (trigger factor) |
| L3G80_06070 | PAL | Del | Cell wall-associated hydrolases (invasion-associated proteins) |
| L3G80_06075 | rex | Del | AT-rich DNA-binding protein |
| L3G80_05015 | copB | Ins | Cation transport ATPase |
| L3G80_10025 | rbcR | Ins | Transcriptional regulator |
| L3G80_11525 | zitR | SNP | Transcriptional regulators |
| L3G80_05095 | mraY | SNP | UDP-N-acetylmuramyl pentapeptide phosphotransferase/ UDP-N-acetylglucosamine-1-phosphase transferase |
| L3G80_03295 | dnaG | SNP | DNA primase (bacterial type) |
| L3G80_03435 | tspO | SNP | Tryptophan-rich sensory protein (mitochondrial benzodiazepine receptor homologue) |
| L3G80_03890 | brnQ | SNP | Branched-chain amino acid permeases |
| L3G80_00800 | ytqA | SNP | Predicted Fe—S oxidoreductase |
| L3G80_02410 | thiT | Ins | Predicted membrane protein |
| L3G80_10565 | yadS | Ins | Predicted membrane protein |
| L3G80_07665 | arlR | Del | Response regulators consisting of a Che-Y-like receiver domain and a winged-helix DNA-binding domain |
| L3G80_02525 | penA | Ins | Cell division protein FtsI/penicillin-binding protein 2 |
| L3G80_02535 | ddl | Ins | D-alanine D-alanine ligase and related ATP-grasp enzymes |

The foregoing are only some preferred embodiments of the present invention, it shall be understood that for those of ordinary skill in the art, some modifications and changes can be made to the present invention without departing from principles of the present invention, and these modifications and changes shall fall within the protection scope of the present invention.

We claim:

1. A *Lactococcus lactis* subsp. *Lactis* A32 strain in a lyophilized form, and a deposit number of the *Lactococcus lactis* subsp. lactic A32 strain is GDMCC No. 62395.

2. A microbial inoculum for producing nisin, wherein active ingredients of the microbial inoculum comprise *Lactococcus lactis* subsp. *lactis* A32 strain (GDMCC No. 62395) According to claim 1.

3. The *Lactococcus lactis* subsp. *lactis* A32 strain according to claim 1, wherein a nisin resistance concentration of the *Lactococcus lactis* subsp. *lactis* A32 strain (GDMCC No. 62395) is 15000 IU/mL.

4. The *Lactococcus lactis* subsp. *lactis* A32 strain according to claim 1, wherein a concentration of nisin titre produced by the *Lactococcus lactis* subsp. *lactis* A32 strain (GDMCC No. 62395) is over 5066.58 IU/mL.

5. A method for producing nisin based on a *Lactococcus lactis* subsp. *lactis* A32 strain in the lyophilized form, comprising following steps:

inoculating bacterial liquid of the *Lactococcus lactis* subsp. *lactis* A32 strain (GDMCC No. 62395) in the lyophilized form into a fermentation medium;

culturing the *Lactococcus lactis* subsp. *Lactis* A32 strain (GDMCC No. 62395) in the fermentation medium;

collecting the fermentation medium and separating nisin.

6. The method for producing nisin based on the *Lactococcus lactis* subsp. *Lactis* A32 strain in the lyophilized form according to claim 5, wherein the fermentation medium is a CM1 medium.

7. The method for producing nisin based on the *Lactococcus lactis* subsp. *Lactis* A32 strain in the lyophilized form according to claim 5, wherein an inoculation amount of the bacterial liquid is 8%~15% (v/v).

8. The method for producing nisin based on the *Lactococcus lactis* subsp. *Lactis* A32 strain in the lyophilized form according to claim 5, wherein temperature for the culturing step is 28~32° C.

9. The method for producing nisin based on the *Lactococcus lactis* subsp. *Lactis* A32 strain in the lyophilized form according to claim 5, wherein time for the culturing step is 20~40 h.

\* \* \* \* \*